United States Patent [19]

Holtkamp, Sr.

[11] Patent Number: Plant 6,106

[45] Date of Patent: Feb. 16, 1988

[54] AFRICAN VIOLET NAMED LITTLE SAPHIRE

[75] Inventor: Reinhold Holtkamp, Sr., Isselburg, Fed. Rep. of Germany

[73] Assignee: Gessellschaftsvertrag uber die Erfindergemeinschaft "OPTIMARA", Rees Haffen, Fed. Rep. of Germany

[21] Appl. No.: 823,475

[22] Filed: Jan. 28, 1986

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

An African violet plant named Little Saphire having a miniature growth habit; single, violet-blue flowers; strong stems which curve toward the center of the plant; early, profuse and continuous flowering, and long-lasting, non-dropping flowers which form a flower head above the leaves.

1 Drawing Figure

The present invention comprises a new and distinct cultivar of African violet plant, botanically known as *Saintpaulia ionantha,* and hereinafter referred to by the cultivar name Little Saphire.

The new cultivar was originated from a cross made in a controlled breeding program in Isselburg, West Germany. The female, or seed parent was a cultivar designated *Saintpaulia schumensis.* The male, or pollen parent was a cultivar designated Z25/S Mini. The new cultivar was given the breeding number H501/Super Mini.

Little Saphire was discovered and selected by me in 1982 as a flowering plant within the progeny of the stated cross in a controlled environment in Isselburg, West Germany. Asexual reproduction of the new cultivar by leaf cuttings, as performed by me at Isselburg, West Germany, has demonstrated that the combination of characteristics as herein disclosed for the new cultivar are firmly fixed and retained through successive generations of asexual reproduction.

Little Saphire has not been observed under all possible environmental conditions. The phenotype may vary significantly with variations in environment such as temperature, light intensity and day length. The following observations, measurements and values describe the new cultivar as grown in Isselburg, West Germany and Nashville, Tenn. under greenhouse conditions which closely approximate those generally used in commercial practice.

The following traits have been repeatedly observed and are determined to be basic characteristics of Little Saphire, which in combination distinguish this African violet as a new and distinct cultivar:

1. Little Saphire will not grow larger than 6–7 cm. tall.
2. Strong wirelike and upright flower stems curving toward the center.
3. First flash of flowers form a tight bouquet above the leaves.
4. Early, profuse and continuous flowering.
5. Each plant carries up to 6 and more upright flower stems, each of which carries 5 and more flowers.
6. Plant saleable 10 to 11 weeks after planting of unrooted shoot.
7. Medium green velvet leaves, slightly hairy.

8. Long-lasting, non-dropping single flowers; occasionally out of the center appears an additional petal.
9. Seed capsule pushes slightly through.
10. Spear-shaped leaves are 1.5 to 2.0 cm. in size.

The accompanying photographic drawing shows a typical specimen plant of the new cultivar grown in a 4 cm. pot. The colors appearing in the photograph are as true as possible with color illustrations of this type. The ruler to the right of the plant is in centimeters, highlighting the miniature size and growth habit of Little Saphire.

In the following description, color references are made to The Royal Horticultural Society Colour Chart (RHS), except where general colors of ordinary significance are referred to. Color values were taken under natural light conditions at approximately 1:00 p.m. in Nashville, Tenn.

Botanical classification: *Saintpaulia ionantha,* Ramat., cv. Little Saphire.

Parentage:

*Male parent.*—Z25/S Mini.

*Female parent.*—*Saintpaulia schumensis.*

PROPAGATION

The new cultivar holds its distinguishing characteristics through successive propagations by leaf cuttings.

PLANT

From 5.5 cm. to 7 cm. tall when grown in pots, and approximately 7–9 cm. in diameter when fully grown.

Leaves:

*Shape.*—Oval to heart-shaped; pointed.

*Diameter.*—15 mm. wide and 23 mm. long.

*Texture.*—Leatherlike.

*Ribs and veins.*—Well pronounced on under side.

*Color (upper side).*—147A.

*Color (under side).*—147C–D.

*Petioles.*—Strong, hairy, brownish-purple.

Flowers:

*Buds.*—Size: 8–10 mm. before opening. Shape: Ball-shaped.

*Sepals.*—Shape: Spear-shaped; five in number. Color: Dark brown.

*Calyx.*—Basifixed.

*Peduncle.*—Character: Strong, upright, hairy. Color: Brownish.

Individual flowers:

*Size.*—35–40 mm. in diameter.

*Shape.*—Single, violet shaped.

*Color (upper side).*—90C–D.

*Color (under side).*—91B.

*Borne.*—Each flower stem carries 6 and more flowers on strong upright peduncles.

Flowering habit: Flowers 8–9 weeks after potting; flower head formed well above leaves; flowers are long lasting and non-dropping; flowers continuously.

Reproductive organs:

*Stamens.*—Two.

*Anthers.*—Two, with four anther cells.

*Filaments.*—2 mm.

*Styles.*—6 mm., dark purple.

Roots: Normally developed, white when young, turning slightly brownish when older.

Disease resistance: Good.

General Observations

Little Saphire is a super miniature violet, which does not grow taller than 6–7 mm. It is a breakthrough in developing a miniature violet with the well known Optimara® characteristics of long-lasting, non-dropping flowers on upright flower stems that form a nice bouquet free standing above the leaves. It flowers early and under good growing conditions it will bloom continuously. The flower is more long-lasting than violets known to date.

I claim:

1. A new and distinct cultivar of African violet named Little Saphire, as illustrated and described, and particularly characterized by its miniature growth habit; single, violet-blue flowers; strong stems which curve toward center of plant; early, profuse and continuous flowering, and by its long-lasting and non-dropping flowers which form a flower head above the leaves.

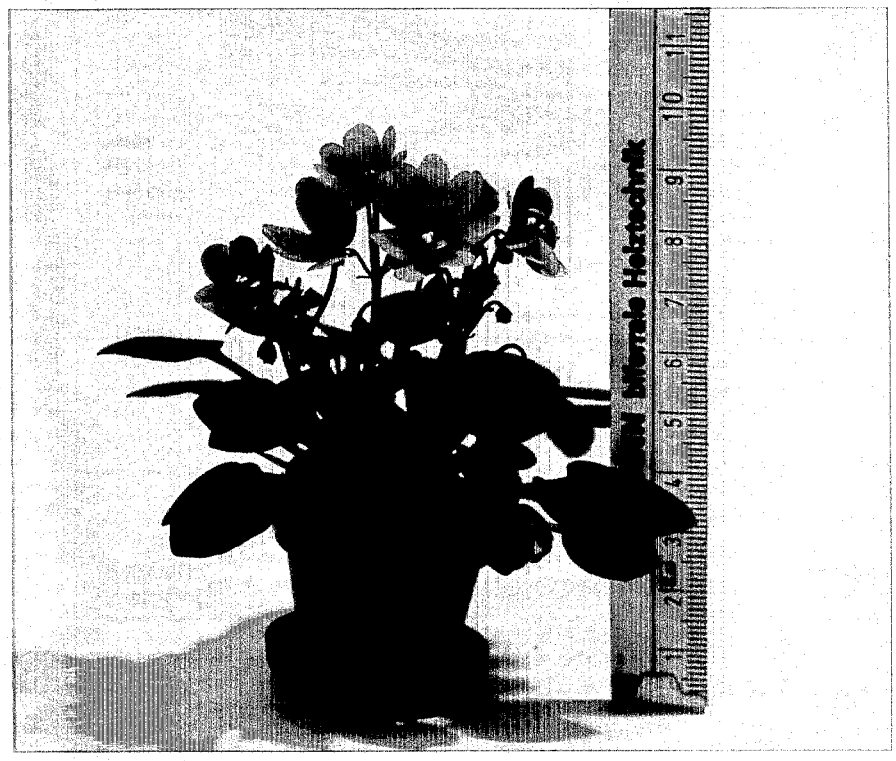

* * * * *